US00PP19775P2

(12) United States Plant Patent
Portilla

(10) Patent No.: US PP19,775 P2
(45) Date of Patent: Feb. 24, 2009

(54) ***JUSTICIA* PLANT NAMED 'ZEBRA'**

(50) Latin Name: *Justicia pictifolia*
Varietal Denomination: Zebra

(76) Inventor: Jose Portilla, Cuenca-Gualaceo Highway, Gualaceo (EC)

( * ) Notice: Subject to any disclaimer, the term of this patent is extended or adjusted under 35 U.S.C. 154(b) by 0 days.

(21) Appl. No.: 12/011,434

(22) Filed: Jan. 25, 2008

Related U.S. Application Data

(60) Provisional application No. 60/872,424, filed on Jun. 15, 2007.

(51) Int. Cl.
*A01H 5/00* (2006.01)

(52) U.S. Cl. ..... Plt./263.1

(58) Field of Classification Search ..... Plt./263.1, Plt./263
See application file for complete search history.

*Primary Examiner*—Annette H Para

(57) ABSTRACT

A new cultivar of *Justicia* plant named 'Zebra' that is characterized by dark green heart shaped leaves with silver stripes and purple flowers.

1 Drawing Sheet

Botanical classification: *Justicia pictifolia.*
Variety denomination: 'Zebra'.

BACKGROUND OF THE INVENTION

The present invention relates to a new and distinct cultivar of *Justicia* plant botanically known as *Justicia pictifolia* and hereinafter referred to by the cultivar name 'Zebra'.

The new cultivar is the product of a breeding program conducted by the inventor in a cultivated area of Gualaceo, Ecuador.

'Zebra' is a hybrid that originated from the hybridization of the female or seed parent an unnamed *Justicia pictifolia* (not patented) and the male or pollen parent an unnamed *Justicia pictifolia* (not patented). The cultivar 'Zebra' was selected by the inventor in 2002 as a single plant within the progeny of the stated cross in Gualaceo, Ecuador.

Asexual reproduction of the new cultivar 'Zebra' first occurred by tissue culture in 2003 in Evergem, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Justicia* cultivar 'Zebra'. These traits in combination distinguish 'Zebra' as a new and distinct cultivar apart from other existing known varieties of *Justicia.*

1. *Justicia* 'Zebra' exhibits dark green leaves with silver stripes.
2. *Justicia* 'Zebra' exhibits heart shaped leaves.
3. *Justicia* 'Zebra' exhibits purple flowers.

The new cultivar 'Zebra' is distinguishable from the unnamed female parent *Justicia pictifolia* by the following characteristics:

1. 'Zebra' exhibits larger leaves.
2. 'Zebra' exhibits longer lasting flowers.
3. 'Zebra' exhibits leaves with a larger number of silver stripes.

The new cultivar 'Zebra' is distinguishable from the unnamed male parent *Justicia pictifolia* by the following characteristics:

1. 'Zebra' exhibits larger leaves.
2. 'Zebra' exhibits longer lasting flowers.
3. 'Zebra' exhibits darker green leaves.

BRIEF DESCRIPTION OF THE DRAWING

The accompanying photograph illustrates the distinguishing traits of *Justicia* 'Zebra'. The plant in the photograph shows an overall view of a 20 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Justicia* cultivar named 'Zebra'. Data was collected in Evergem, Belgium from 20 week old glass greenhouse grown plants in 6.6 cm. diameter containers. The time of year was Fall and the temperature range was 22–32 degrees Centigrade during the day and 13–22 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Zebra' has not been tested under all possible conditions and phenotypic differences may be observed with variations in environmental, climatic, and cultural conditions, however, without any variance in genotype.

Botanical classification: *Justicia* 'Zebra'.
Use: Ornamental Annual.
Parentage: 'Zebra' is a hybrid plant that resulted from the hybridization of the following parent plants:
*Female parent.*—An unnamed *Justicia pictifolia* cultivar.
*Male parent.*—An unnamed *Justicia pictifolia* cultivar.

Vigor: Moderate.
Growth habit: Upright.
Plant shape: Elliptic.
Suitable container size: 6.6 cm. pots.
Height: 23.2 cm. in height.
Width: 15.7 cm. in width.
Low temperature tolerance: USDA Zone 10.
High temperature tolerance: 40° Centigrade.
Propagation: Terminal cuttings.
Time to initiate roots: 10–14 days to initiate roots at 20° Centigrade.
Time to produce a rooted cutting or liner: 28 days at 20° Centigrade.
Crop time: 20 weeks are required to produce a finished flowering plant.
Growth rate: Approximately 15 cm. per month in spring.
Root system: Fine and fibrous.
Stem:
*Branching habit.*—Flowering stems grow from the base, no lateral branches.
*Average number of main stems.*—3.
*Pinching.*—Not Required.
*Stem diameter.*—3.5 mm. in diameter.
*Stem length.*—6.1 cm. in length.
*Stem branch strength.*—Very strong.
*Stem color.*—147A with nodes 138A.
*Stem shape.*—Smooth and glossy.
*Pubescence.*—Absent.
*Internode length.*—3.6 cm. between nodes.
*Aspect.*—Rounded.
*Strength.*—Moderate to high.
*Other characteristics.*—Diameter of stem is slightly larger at the nodes; 4.5 mm.
Foliage:
*Texture.*—Dull, slightly rugose, and leathery.
*Leaf arrangement.*—Opposite.
*Compound or single.*—Single.
*Quantity of leaves per stem.*—8.
*Leaf shape.*—Cordate.
*Leaf apex.*—Apiculate.
*Leaf base.*—Cordate.
*Leaf length.*—8.2 cm. in length.
*Leaf width.*—6.6 cm. in width.
*Pubescence.*—Absent.
*Leaf margin.*—Entire.
*Young leaf color* (*lower surface*).—147B.
*Young leaf color* (*upper surface*).—137A; intervein parts 198D.
*Mature leaf color* (*lower surface*).—In between 138B and 147B.
*Mature leaf color* (*upper surface*).—139A; intervein parts 198C to 198D.
*Vein color* (*under surface*).—146A.
*Vein color* (*upper surface*).—138B to 147B.
*Venation pattern.*—Pinnate.
*Leaf attachment.*—Petiolate.
*Petiole dimensions.*—1 cm. in length; 4 mm. in width; 2.5 mm. in height.
*Petiole color.*—147B.
Flower:
*Inflorescence arrangement.*—Terminal raceme.
*Flowering habit.*—Continuous.
*Quantity of flowers per stem.*—3.
*Quantity of flower buds per stem.*—12.
*Quantity of flowers and buds per plant.*—12.
*Natural flowering season.*—Autumn and winter.
*Fragrance.*—None.
*Flower bud length.*—8 mm. in length.
*Flower bud diameter.*—3 mm. in diameter.
*Flower bud shape.*—Obovate.
*Bud color.*—144C, tip N187C to N187D; base 148A with N186C.
*Rate of bud opening.*—5 days.
*Flower aspect.*—Upright to slightly outward.
*Flower shape.*—Labiate.
*Flower dimension.*—1.3 cm. in diameter and 1.6 cm. in height.
*Flower longevity.*—Approximately 7 days.
*Petal appearance.*—Glossy.
*Petal texture.*—Has small glandular hairs, 0.2 mm.
*Number of petals.*—2.
*Fused or unfused.*—Only the lower half is fused.
*Petal appearance.*—Smooth.
*Petal shape.*—Upper lip: Obovate. Lower lip: Spathulate.
*Petal margin.*—Entire, lower half fused.
*Petal apex.*—Upper lip: Acute. Lower lip: Obtuse.
*Petal length.*—1.8 cm. in length.
*Petal width.*—Upper lip: 7 mm. Lower lip: 1.2 cm.
*Petal color when opening* (*upper side*).—Upper lip: 145C with dots 179B to 179C. Lower lip: 64C to 64D, base is lighter, 155A; has darker dots, 64D.
*Petal color when opening* (*under side*).—Upper lip: 145C to 145D with dots, 179C to 179D. Lower lip: 69C; base 145C to 145D.
*Petal color fully opened* (*upper side*).—Upper lip: 145C with dots, 179B to 179C. Lower lip 69C; base 145C to 145D.
*Petal color fully opened* (*under side*).—Upper lip: 145C to 145D with dots, 179C to 179D. Lower lip: 69C, base 145C to 145D.
*Petal color fading to.*—Upper lip not fading, lower lip fading to 71A to 71C.
*Self-cleaning or persistent.*—Self-cleaning.
Sepals:
*Number of sepals.*—Two rows of 4, 8 total.
*Sepal aspect.*—Upright, rigid.
*Sepal shape.*—Narrow ovate, fused into a campanulate shape.
*Sepal margin.*—Entire.
*Sepal apex.*—Acute.
*Sepal base.*—Fused cuneate.
*Sepal surface.*—Dull.
*Sepal dimensions.*—7 mm. in length and 1.5 mm. in width.
*Young sepal color* (*upper side*).—148A; has some N186C.
*Young sepal color* (*under side*).—148B to 148C.
*Mature sepal color* (*upper side*).—146B, base (lower 4 sepals) 187A.
*Mature sepal color* (*under side*).—146C, base (lower 4 sepals) 187B.
Calyx:
*Calyx shape.*—Campanulate.
*Calyx dimension.*—7 mm. in length and 4 mm. in diameter.
Peduncle:
*Peduncle dimensions.*—11.5 cm. in length and 2 mm. in diameter.
*Peduncle aspect.*—Upright.
*Peduncle angle.*—0°.

*Peduncle color.*—146A, covered with glandular hairs 0.2 mm, 187A to 187B.

*Peduncle strength.*—Moderate.

Reproduction organs:

*Stamen number.*—2.

*Anther shape.*—Kidney-shaped, flat, perpendicular to filament.

*Anther dimensions.*—9 mm. in length and 4 mm. in width.

*Anther color.*—144B.

*Amount of pollen.*—Very low.

*Pollen color.*—151B to 151D.

*Pistil number.*—1.

*Pistil dimensions.*—1.4 cm. in length.

*Stigma shape.*—Club-shaped.

*Stigma color.*—144C.

*Style length.*—1.3 cm.

*Style color.*—144C.

*Ovary color.*—143B.

Disease and pest resistance: Plants of the new cultivar have not been observed for disease and pest resistance.

What is claimed is:

1. A new and distinct variety of *Justicia* plant named 'Zebra' as described and illustrated.

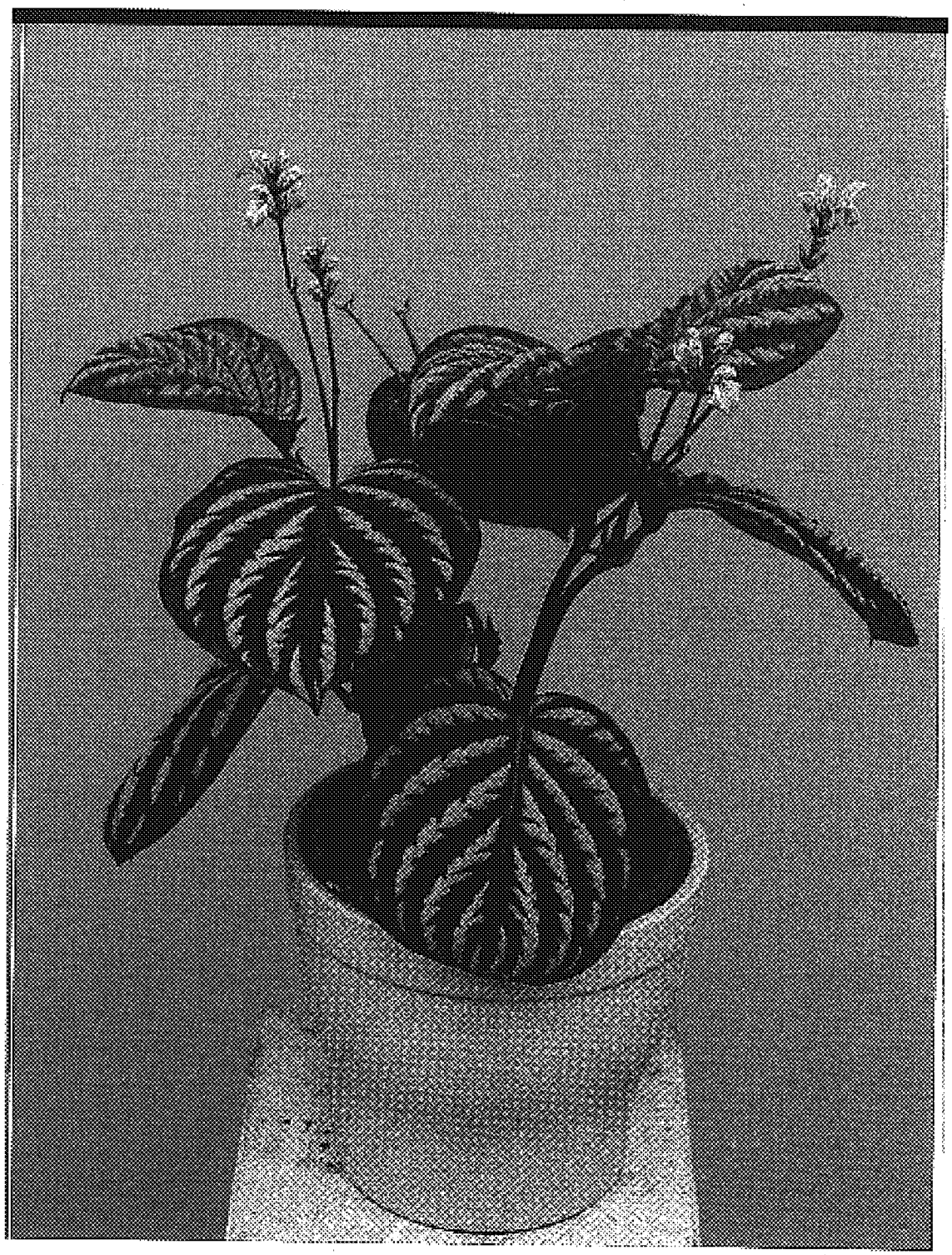

* * * * *